United States Patent [19]

Grimmel et al.

[11] Patent Number: 5,142,032
[45] Date of Patent: Aug. 25, 1992

[54] HUMAN PAPILLOMAVIRUS TYPE 41 DNA

[75] Inventors: Margita Grimmel, Neustadt; Ethel-Michele de Villiers, Hirschberg, both of Fed. Rep. of Germany

[73] Assignee: Behringwerke Aktiengesellschaft, Marburg/Lahn, Fed. Rep. of Germany

[21] Appl. No.: 216,913

[22] Filed: Jul. 8, 1988

[30] Foreign Application Priority Data

Jul. 11, 1987 [DE] Fed. Rep. of Germany ....... 3722968

[51] Int. Cl.$^5$ .............. C12N 15/37; C12N 7/00; C12Q 1/70
[52] U.S. Cl. .................. 536/27; 435/235.1; 435/320.1; 435/5
[58] Field of Search ............ 435/172.1, 172.3, 68, 435/70, 235; 536/27

[56] References Cited

U.S. PATENT DOCUMENTS 4,849,331 7/1989 Lorincz ................ 435/5
4,849,334 7/1989 Lorincz ................ 435/5

OTHER PUBLICATIONS

CA 134770s (V.106) (1987).
CA 193679s (V.106) (1987).
Grimmel, M. et al. 1988, *Int. J. Cancer* vol. 41 pp. 5–9.
DeVilliers, E. 1989, *Journal of Virology* vol. 63 pp. 4898–4903.
Radloff, R., et al., Proc. Nat. Acad. Sci. 57:1514–1521 (1967).
Southern, E. M., J. Mol. Biol. 98:503–517 (1975).
Messing J., et al., Proc. Nat. Acad. Sci. 74, No. 9:3642–3646 (1977).
Birnboim, H. C., et al., Nucleic Acids Research, vol. 7, No. 6:1513–1523 (1979).
Gissmann, L., et al., Int. J. Cancer 29:143–146 (1982).
Yanisch-Perron, C., et al., Gene 33:103–109 (1985).
Fuchs, P., et al., Journal of Virology 58:626–634 (1986).
Hausen, H., et al., The Papovaviridae 2:245–263 Plenum Publishing Corporation (1987).

*Primary Examiner*—Richard A. Schwartz
*Assistant Examiner*—Mary E. Mosher
*Attorney, Agent, or Firm*—Finnegan, Henderson, Farabow, Garrett and Dunner

[57] ABSTRACT

The invention relates to isolation of human papillomavirus type 41, partial characterization of its genome and its cloning in pUC 19. This opens up an access to early diagnosis of skin tumors associated with HPV 41.

1 Claim, 1 Drawing Sheet

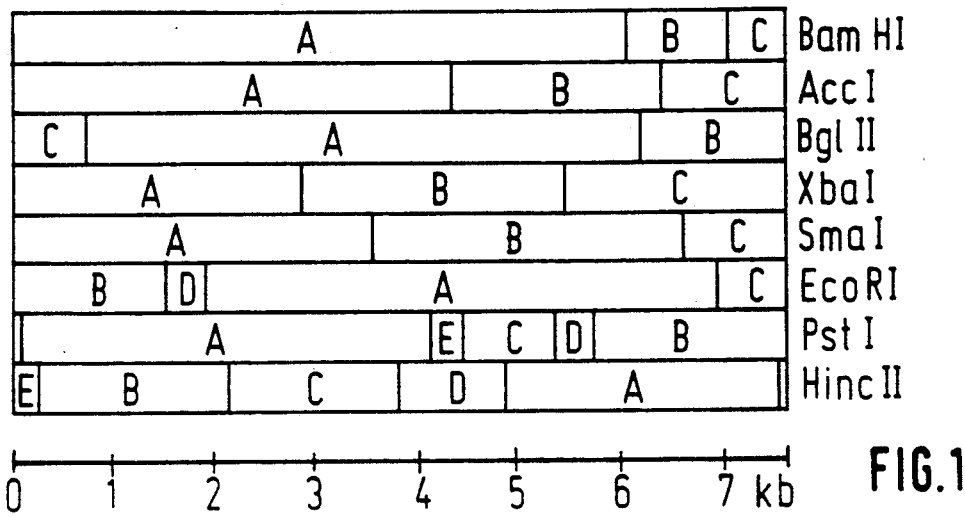
FIG.1
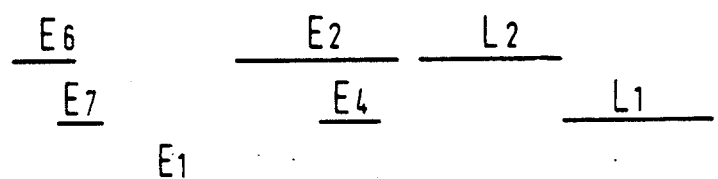
FIG.2
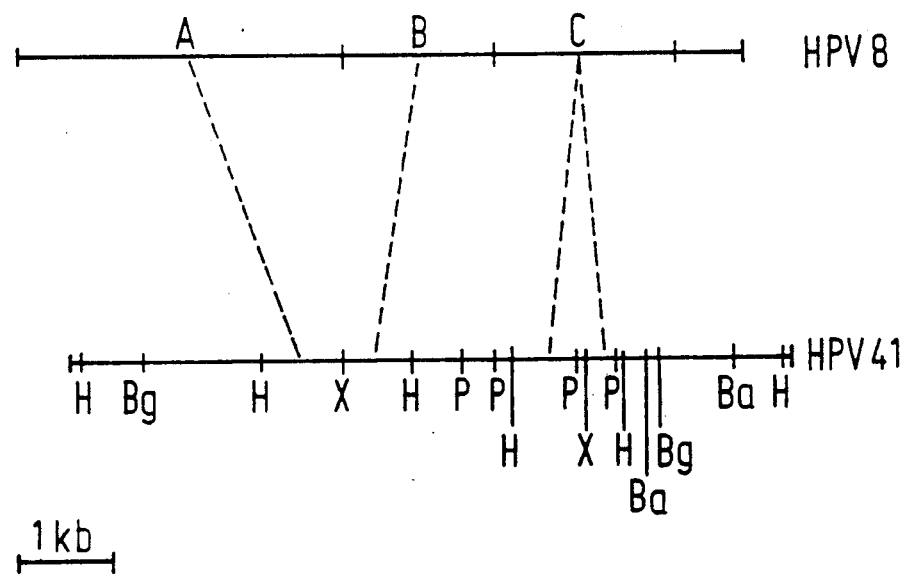

HUMAN PAPILLOMAVIRUS TYPE 41 DNA

DESCRIPTION

Human papillomaviruses (HPV) form a group of about 40 different types (zur Hausen, H. and Schneider, A. (1987), The Papillomaviruses, Howley, P. M. and Salzmann, N. P. (editors), currently being printed). HPV was discovered in connection with benign (warts and condylomata in the genital region) and malignant (carcinomas of the skin and vagina) epithelial neoplasms. Papillomaviruses cannot be multiplied by culture. The use of human papillomavirus type 41 DNA (HPV 41 DNA) as a diagnostic and the production of expression products, their use as antigens, the isolation of antibodies and the preparation of corresponding diagnostics and therapeutics thus require genetic engineering processes.

The invention is based on the isolation for the first time of HPV 41, a partial characterization of its genome and cloning in pUC 19. This opens up an access to early diagnosis of skin tumors associated with HPV 41.

BRIEF DESCRIPTION OF THE FIGURES

FIG. 1 corresponds to a physical genome chart of the HPV 41 molecule. The single KpnI cleavage site was used to linearize the HPV 41 DNA. HPV 41 DNA was first cleaved from a vector by the restriction enzyme BamHI. The HPV 41 DNA was then digested with the restriction endonucleases AccI, BglII, XbaI, SmaI, EcoRI, PstI and HincII. The fragments produced by endonuclease cleavage were labeled, with "A" designated as the largest fragment produced, "B" the next largest, with each smaller fragment designated by the next letter of the alphabet. The results appear in FIG. 1.

FIG. 2 shows the colinearity of HPV 41 DNA with HPV 8 DNA on the basis of hybridization experiments. The results of the cleavage of the HPV 41 DNA with the restriction endonucleases HincII, BglII, XbaI, PstI, and BamHI compared with the HPV 8 DNA is shown at the bottom of FIG. 2.

The invention is defined in the patent claims. Further embodiments of the invention are described in more detail below.

Cloning of HPV 41 made comparison with 40 other HPV possible. HPV 7, 8, 10, 17, 27, 29, 30 and 33 are distantly related, the colinearity of HPV 41 with HPV 8 having been demonstrated (FIG. 2) and physical genome charts having been drawn up for restriction enzyme cleavages (FIG. 1).

This has thus provided access to testing of neoplasias, in particular carcinomas of the skin, for the occurrence of HPV 41 and, if appropriate, of attempting therapy via antibodies to HPV 41 proteins.

EXAMPLES

1. Isolation of episomal HPV 41 DNA

Biopsies from wart tissue from three different body areas of a 15-year old girl were deep-frozen at −70° C. and stored immediately after being obtained. High-molecular DNA was isolated therefrom as described (Gissmann et al. (1982), Int. J. Cancer 29, 143–146). Circular closed double-stranded DNA was obtained from the cellular DNA mentioned in accordance with the method of Radloff et al. (1967) Proc. Nat. Acad. Sci. 57, 1514–1521, about 10 $\mu$g of DNA being centrifuged in a 50 Ti rotor (Beckmann Corp.) at 45,000 rpm for 48 hours in CsCl (density 1.56 g/ml) with the addition of 600 $\mu$g/ml of ethidium bromide. the fractions with a density of 1.59–1.60 then being collected. Alternatively, episomal HPV 41 DNA of whole DNA from the same biopsy material could be detected in agarose gels stained with ethidium bromide (1% of agarose (Seakem ME) in 40 mM tris-acetate and 2 mM EDTA (pH 7.8)) and isolated therefrom.

2. Cloning of HPV 41 in plasmid pUC 19

The known plasmid pUC 19 (Yanish-Perron et al. (1985), Gene 33, 113–119) was chosen as the cloning vector. Circularly closed double-stranded DNA was cloned in pUC 19 after cleavage with BamHI (Maniatis et al. (1982), Molecular Cloning: a Laboratory Manual; Cold Spring Harbor Laboratory Press, New York). Recombinant clones were identified in the $\beta$-galactosidase test (Messing et al. (1977), Proc. Nat. Acad. Sci. USA 74, 3642–3646) and DNA fragments ligated in analyzed by high-speed DNA extraction (Birnboim, H. L. and Doly. (1979), Nucl. Acids Res. 7, 1513–1523).

Two recombinants were obtained, one of which, K 10, contained an insertion of 6.6 kb, and the other of which, K 6, contained an insertion of 0.98 kb. The homology of these cloned sequences is demonstrated by hybridization with episomal DNA from biopsy material.

3. Physical genome charts of HPV 41

HPV 41 DNA separated off from the vector by BamHI cleavage was digested with the restriction endonucleases AccI, BglII, XbaI, SmaI, EcoRI, PstI and HincII and the corresponding physical genome charts were drawn up by generally known methods. The result is summarized in FIG. 1, the sole KpnI cleavage point serving to linearize the HPV 41 molecule.

4. Comparison with other HPV

The DNA of the HPV 41 genome was compared with the DNA's of 40 obtainable types of HPV by means of DNA/DNA hybridization under various stringencies (E. M. Southern (1975), J. Mol. Biol. 98, 503–517). Under conditions of high stringency (melting temperature Tm −20° C.), HPV 41 K 10-DNA partly hybridizes with HPV 29-DNA. The DNA of the K 6 clone hybridizes only under low stringency (Tm −40° C.) with HPV 3- and 13under DNA.

The colinearity with HPV 8 on the basis of hybridization experiments is shown in FIG. 2.

Knowing the HPV 8 DNA sequence (Fuchs et al. (1986), J. Virol. 58, 626–634), the open reading frames of HPV 41 are deducible and thus the HPV 41 proteins are obtainable by generally known methods for subcloning clones K 10 and K 6 with subsequent expression in prokaryotic or eukaryotic expression systems.

The plasmids HPV 41 clone K6 and K10 were deposited (in *E. coli*) on 3.7.1987 at the German Collection of Microorganisms under numbers DSM 4174P (for K6) and DSM 4175P (for K10).

We claim:

1. Isolated HPV 41DNA characterized by the restriction enzyme cleavage pattern of FIG. 1 and contained in clones K 10 and K6.

* * * * *

UNITED STATES PATENT AND TRADEMARK OFFICE
CERTIFICATE OF CORRECTION

PATENT NO. : 5,142,032

DATED : August 25, 1992

INVENTOR(S) : Grimmel et al.

It is certified that error appears in the above-identified patent and that said Letters Patent is hereby corrected as shown below:

Claim 1, column 2, line 64, "4 1DNA" should read --41 DNA--;

line 66, "K6" should read --K 6--.

Signed and Sealed this

First Day of February, 1994

*Attest:*

BRUCE LEHMAN

*Attesting Officer*     *Commissioner of Patents and Trademarks*